United States Patent
Dube et al.

(10) Patent No.: US 11,766,438 B2
(45) Date of Patent: Sep. 26, 2023

(54) PHARMACEUTICAL COMPOSITIONS OF TOFACITINIB FOR ORAL ADMINISTRATION

(71) Applicant: Slayback Pharma LLC, Princeton, NJ (US)

(72) Inventors: Sushant Omprakash Dube, Navi Mumbai (IN); Purushottam Dattatraya Kulkarni, Aurangabad (IN); Purushottam Sakhahari Pattewar, Hyderabad (IN); Sumitra Ashokkumar Pillai, Hyderabad (IN)

(73) Assignee: SLAYBACK PHARMA LLC, Princeton, NJ (US)

( * ) Notice: Subject to any disclaimer, the term of this patent is extended or adjusted under 35 U.S.C. 154(b) by 5 days.

(21) Appl. No.: 17/239,007

(22) Filed: Apr. 23, 2021

(65) Prior Publication Data

US 2021/0338677 A1    Nov. 4, 2021

(30) Foreign Application Priority Data

Apr. 24, 2020 (IN) .............................. 202041017604

(51) Int. Cl.
| | |
|---|---|
| A61K 31/277 | (2006.01) |
| A61K 31/519 | (2006.01) |
| A61K 9/00 | (2006.01) |
| A61K 47/12 | (2006.01) |
| A61K 47/40 | (2006.01) |
| A61K 47/14 | (2017.01) |
| A61K 47/26 | (2006.01) |
| A61K 47/20 | (2006.01) |
| A61K 9/08 | (2006.01) |

(52) U.S. Cl.
CPC .......... *A61K 31/519* (2013.01); *A61K 9/0053* (2013.01); *A61K 9/08* (2013.01); *A61K 47/12* (2013.01); *A61K 47/14* (2013.01); *A61K 47/20* (2013.01); *A61K 47/26* (2013.01); *A61K 47/40* (2013.01)

(58) Field of Classification Search
None
See application file for complete search history.

(56) References Cited

U.S. PATENT DOCUMENTS

| | | |
|---|---|---|
| RE41,783 E | 9/2010 | Blumenkopf et al. |
| 9,937,181 B2 | 4/2018 | Herbig et al. |
| 10,639,309 B2 | 5/2020 | Herbig et al. |
| 2019/0231782 A1* | 8/2019 | Chen .................. A61K 31/519 |

FOREIGN PATENT DOCUMENTS

| | | | |
|---|---|---|---|
| CA | 3044091 A1 | | 12/2019 |
| CN | 106389371 A | | 2/2017 |
| CN | 109893502 A | * | 6/2019 |
| JP | 2016199602 A | | 12/2016 |
| WO | 2015/198225 A1 | | 12/2015 |
| WO | 2017/017542 A1 | | 2/2017 |
| WO | 2017/029587 A1 | | 2/2017 |
| WO | 2019/224058 A1 | | 11/2019 |
| WO | 2021/014453 A1 | | 1/2021 |
| WO | 2021/038014 A1 | | 3/2021 |

OTHER PUBLICATIONS

Younis et al. (Preformulation and Evaluation of Tofacitinib as a Therapeutic Treatment for Asthma, AAPS PharmSciTech (2019) 20: 167 (Year: 2019).*

* cited by examiner

*Primary Examiner* — Layla Soroush
(74) *Attorney, Agent, or Firm* — Birch, Stewart, Kolasch & Birch, LLP

(57) ABSTRACT

The present invention relates to liquid pharmaceutical compositions of tofacitinib or its pharmaceutically acceptable salts thereof, suitable for oral administration, that are stable under varying storage conditions for extended periods of time. The present invention also relates to methods of treating auto-immune disorders using the stable liquid pharmaceutical compositions of tofacitinib. A stable liquid pharmaceutical composition of tofacitinib according to the invention comprises of (a) tofacitinib at a concentration of about 1 mg/mL or more; (b) a pharmaceutically acceptable liquid vehicle; (c) at least one anti-oxidant; and (d) optionally one or more other pharmaceutically acceptable excipients.

10 Claims, No Drawings

PHARMACEUTICAL COMPOSITIONS OF TOFACITINIB FOR ORAL ADMINISTRATION

CROSS-REFERENCE TO RELATED APPLICATIONS

This application claims foreign priority to Indian Application No. IN, 202041017604 filed on Apr. 24, 2020, which is incorporated herein by reference in its entirety.

FIELD OF THE INVENTION

The present invention relates to liquid pharmaceutical compositions of tofacitinib or its pharmaceutically acceptable salts thereof, suitable for oral administration, that are stable under varying storage conditions for extended periods of time. The present invention also relates to methods of treating auto-immune disorders using the stable liquid pharmaceutical compositions of tofacitinib.

BACKGROUND OF THE INVENTION

Tofacitinib citrate is a compound with the chemical name (3R,4R)-4-methyl-3-(methyl-7H-pyrrolo[2,3-d]pyrimidin-4-ylamino)-β-oxo-1-piperidinepropanenitrile, 2-hydroxy-1,2,3-propanetricarboxylate (1:1), and the following chemical structure:

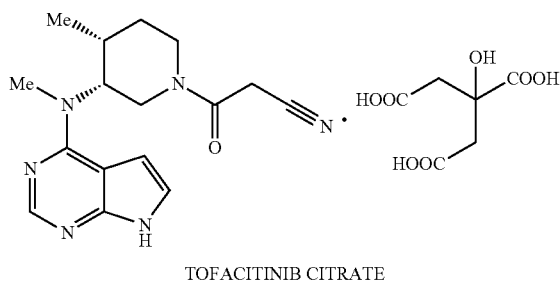 [SMILES: C[C@@H]1CCN(C(=O)CC#N)C[C@@H]1N(C)c1ncnc2[nH]ccc12 ; O=C(O)CC(O)(CC(=O)O)C(=O)O]

TOFACITINIB CITRATE

Tofacitinib is an inhibitor of Janus Kinase (JAK) enzyme. Pharmaceutical compositions of tofacitinib are approved in the US for the treatment of rheumatoid arthritis (RA), psoriatic arthritis (PA), ulcerative colitis (UC) and polyarticular course juvenile idiopathic arthritis (pcJIA). Use of tofacitinib compositions for other indications such as treatment of inflammatory bowel disease, other immunological diseases, as well as for the prevention of organ transplant rejection is currently being investigated. Tofacitinib citrate is characterized as a Biopharmaceutical Classification System (BCS) class III compound, which means that it has high aqueous solubility and moderate permeability. Solubility of tofacitinib citrate is pH dependent; it ranges from 3.48 to 28 mg/mL in aqueous solution of pH 1 to 3.9, and from 0.20 to 0.59 mg/mL in aqueous solution of pH 4.53 to 8. The solubility of tofacitinib citrate at 25° C. in aqueous solutions decreases with an increase in pH.

Tofacitinib compositions in the US are marketed under the brand names XELJANZ® and XELJANZ® XR. XELJANZ® is available in the form of immediate-release film coated tablets (5 mg, 10 mg) and oral solution (1 mg/mL). XELJANZ® XR is available as sustained or extended release tablets (11 mg, 22 mg). Each tablet of XELJANZ® contains 5 mg tofacitinib or 10 mg tofacitinib. Patients with polyarticular course juvenile idiopathic arthritis (pcJIA) may be prescribed with XELJANZ® tablet/XELJANZ® oral solution at a recommended dose of 5 mg twice daily or weight-based equivalent twice daily.

As with any solid oral dosage forms, currently available tablet formulations of tofacitinib have certain disadvantages with respect to their suitability for pediatric and geriatric patients. First, administration of the solid dosage tablets is considered difficult in pediatric and geriatric populations because of the patients' often decreased or low ability of swallow. In order to overcome this issue, caregivers or parents often administer solid formulations using unscientific, ineffective methods. For example, tablets or powdered drugs are dissolved in a suitable liquid base to "create" an oral liquid. The tablets are crushed and the resulting powder added to water or juice; sprinkled onto solid food like apple sauce or pudding. Administration of the solid drugs using these methods is unreliable, tedious and unhygienic.

Second, solid dosage forms are difficult to administer in the absence of dose dependent formulations for pediatric patients. Formulating and selling a dose dependent pediatric formulation is often not a priority for pharmaceutical companies. Consequently, adult formulations are often administered to children on an off-label basis by "breaking" or modifying the solid forms, which could lead to bioavailability issues due to dose errors or inaccurate dosing. This is especially true in cases where small amounts of active ingredients are involved, as in the case of XELJANZ®. Further, tampering of the drug formulation could also lead to stability issues.

Third, palatability is a major concern for administration of solid oral formulations to pediatric patients.

The above concerns may be remedied by preparing a liquid oral formulation of tofacitinib. Liquid dosage forms such as solutions, syrups or suspensions increase palatability by masking the disagreeable taste of the active ingredient. They are easy, safe and precise for administration to patients with compromised swallowing ability. If at all required, liquid formulations allow easy and accurate division to smaller doses when dose dependent formulations for pediatric patients are unavailable. Thus, there is a need to develop a stable tofacitinib formulation in the form of a liquid.

However, formulation of tofacitinib into a liquid formulation that is stable for extended periods of time has not been previously possible because of stability issues. Tofacitinib is prone to hydrolytic and oxidative degradation products which may have a significant impact on drug safety, quality and efficacy. For example, the amide and cyano groups of the 3-oxopropanenitrile moiety of tofacitinib are susceptible to hydrolysis in acidic and basic environments. These groups are also known to degrade at higher temperatures. Pyrrole ring double bond of tofacitinib is intrinsically sensitive to oxidation. Further, exposure to light and variations in pH also affects the stability of tofacitinib. Overall, the chemical moieties on tofacitinib make it susceptible to degradation in aqueous environment.

The present invention resolves the above concerns by providing a liquid pharmaceutical composition of tofacitinib for oral administration which is safe, therapeutically effective, easy to administer, palatable, and stable for extended periods of time, under varying storage conditions.

SUMMARY OF THE INVENTION

The present invention provides a stable liquid pharmaceutical composition of tofacitinib suitable for oral administration comprising: (a) tofacitinib at a concentration of about 1 mg/mL or more; (b) a pharmaceutically acceptable liquid vehicle; and (c) optionally, one or more pharmaceutically acceptable excipients. The composition as described above, wherein pharmaceutically acceptable liquid vehicle is selected from a group consisting of water, purified water, isopropyl alcohol, methanol, acetone, ethanol, 1-propanol, butanediol or combinations thereof.

The composition as described above, wherein pharmaceutically acceptable excipients are selected from a group consisting of stabilizers, solubilizers, pH adjusting agents, buffering agents, thickening agents, anti-oxidants, chelating agents, preservatives, flavoring agents, sweetening agents, coloring agents and mixtures thereof.

Another aspect of the present invention provides a stable liquid pharmaceutical composition of tofacitinib suitable for oral administration comprising: (a) tofacitinib at a concentration of about 1 mg/mL or more; (b) a pharmaceutically acceptable liquid vehicle; and (c) at least one anti-oxidant.

The composition as described above, wherein pharmaceutically acceptable liquid vehicle is selected from group consisting of water, purified water, isopropyl alcohol, methanol, acetone, ethanol, 1-propanol, butanediol or combinations thereof.

The composition as described above, wherein anti-oxidant is selected from group consisting of acetone, sodium bisulfate, ascorbic acid, ascorbyl palmitate, citric acid, tartaric acid, glycine, L-cysteine hydrochloride, L-methionine, butylated hydroxy anisole (BHA), butylated hydroxytoluene (BHT), hydro phosphorous acid, monothioglycerol, propyl gallate, sodium ascorbate, sodium citrate anhydrous, sodium citrate dihydrate, sodium sulfide, sodium sulfite, sodium bisulfite, sodium formaldehyde sulfoxylate, thioglycolic acid, sodium metabisulfite.

The composition as described above, wherein the anti-oxidant is present in a concentration ranges from about 0.01% to about 50% w/w of total composition.

The composition as described above, wherein the anti-oxidant is present in concentration of about 0.05% w/w of total composition.

The composition as described above, wherein the anti-oxidant is tartaric acid.

The composition as described above, wherein the tartaric acid is present in concentration of about 0.05% w/w of total composition.

The composition as described above, wherein the tartaric acid is present in an amount of 0.5 mg/mL.

The composition as described above, wherein said composition is stable for at least 6 months at 25° C./60% RH.

Another aspect of the invention provides a stable liquid pharmaceutical composition of tofacitinib suitable for oral administration comprising: (a) tofacitinib at a concentration of about 1 mg/mL or more; (b) a pharmaceutically acceptable liquid vehicle; and (c) at least one anti-oxidant; and (d) optionally, one or more other pharmaceutically acceptable excipients, wherein the pharmaceutical composition is stable for at least 6 months at 25° C./60% RH.

A stable liquid pharmaceutical composition of tofacitinib suitable for oral administration comprising: (a) tofacitinib at a concentration of about 1 mg/mL or more; (b) a pharmaceutically acceptable liquid vehicle; (c) one or more other pharmaceutically acceptable excipients, wherein the pH of pharmaceutical composition ranges from about 2.5 to about 7.5.

The stable liquid pharmaceutical composition as described above, wherein the pH of pharmaceutical composition ranges from about 4 to about 4.6.

Another aspect of the invention provides a stable liquid pharmaceutical composition of tofacitinib suitable for oral administration comprising: (a) tofacitinib at a concentration of about 1 mg/mL or more; (b) a pharmaceutically acceptable liquid vehicle; and (c) optionally, one or more other pharmaceutically acceptable excipients, wherein the pH of pharmaceutical composition ranges from about 4 to about 5, wherein the level of Impurity-B in the composition is less than about 0.5% w/w as measured by HPLC when stored at 25° C./60% RH or 40° C./75% RH for at least a period of 6 months.

Another aspect of the invention provides a stable liquid pharmaceutical composition of tofacitinib suitable for oral administration comprising: (a) tofacitinib at a concentration of about 1 mg/mL or more; (b) a pharmaceutically acceptable liquid vehicle; (c) at least one anti-oxidant; and (d) optionally, one or more other pharmaceutically acceptable excipients, wherein the pH of pharmaceutical composition ranges from about 4 to about 5, wherein the total level of impurities in the composition is less than about 3% w/w as measured by HPLC when stored at 25° C./60% RH or 40° C./75% RH for at least a period of 6 months.

Another aspect of the invention provides a stable liquid pharmaceutical composition of tofacitinib suitable for oral administration comprising: (a) tofacitinib at a concentration of about 1 mg/mL or more; (b) a pharmaceutically acceptable liquid vehicle; and (c) optionally, one or more other pharmaceutically acceptable excipients, wherein the pH of pharmaceutical composition ranges from about 4 to about 5, wherein liquid pharmaceutical composition is free from precipitation when stored at 25° C./60% RH for at least a period of 6 months.

Another aspect of the invention provides a stable liquid pharmaceutical composition of tofacitinib suitable for oral administration comprising: (a) tofacitinib at a concentration of about 1 mg/mL or more; (b) purified water; and (c) tartaric acid; and (d) optionally, one or more other pharmaceutically acceptable excipients.

Another aspect of the invention provides a stable liquid pharmaceutical composition of tofacitinib suitable for oral administration comprising: (a) tofacitinib at a concentration of about 1 mg/mL or more; (b) purified water and (c) 0.5 mg/mL tartaric acid, wherein the pH of pharmaceutical composition ranges from about 4 to about 4.6, wherein the level of total impurities in the composition is less than about 3% w/w as measured by HPLC, when stored at 25° C./60% RH or 40° C./75% RH for a period of at least 6 months.

Another aspect of the invention provides a stable liquid pharmaceutical compositions of tofacitinib suitable for oral administration comprises (a) tofacitinib at a concentration of about 1 mg/mL or more; (b) a pharmaceutically acceptable liquid vehicle and c) optionally one or more other pharmaceutically acceptable excipients, wherein the pH of pharmaceutical composition ranges from about 4 to about 4.6, wherein the level of Impurity-B in the composition is less than about 0.5% w/w, as measured by HPLC when stored at 25'C/60% RH or 40° C./75% RH for a period of at least 6 months.

A stable liquid composition suitable for oral administration comprising: (a) tofacitinib at a concentration of about 1 mg/mL or more; (b) a pharmaceutically acceptable liquid vehicle; (c) at least one anti-oxidant; and (d) one or more other pharmaceutically acceptable excipients, wherein the weight ratio of anti-oxidant to tofacitinib is from about 0.1:1 to about 1:10, preferably about 1:3.

DETAILED DESCRIPTION OF THE INVENTION

Unless defined otherwise, all the technical and scientific terms used herein have the same meanings as commonly known by a person skilled in the art. In case of conflict, the definitions provided herein will prevail. Unless specified otherwise, all the percentages, portions and ratios in the present invention are on weight basis.

The terms "about" and "approximate", when used along with a numerical variable, generally means the value of the variable and all the values of the variable within an experimental error (e.g. 95% confidence interval for the mean) or within a specified value ±10% or within a broader range.

"Tofacitinib" according to the disclosure is tofacitinib free base or its pharmaceutically acceptable salts, solvates or hydrates thereof. In principle, any crystalline form of tofacitinib or amorphous form of tofacitinib may be used for manufacturing the pharmaceutical composition of the present invention.

The term "pharmaceutically acceptable" substances means those, which, according to a common medical judgment, are suitable to be in contact with a tissue of a patient without any inappropriate toxicity, irritation, allergic response, etc., have a reasonable balance between advantages and disadvantages, and can be applied to its target use effectively.

The term "pharmaceutically acceptable salt" refers to tofacitinib salts which are formed with inorganic or organic acids. Such salts include, but are not limited to, citrate salt, hydrochloride salt, hydrobromide salt, oxalate salt, nitrate salt, sulfate salt, phosphate salt, fumarate salt, succinate salt, maleate salt, besylate salt, tosylate salt, palmitate salt and tartrate salt. Preferably, the pharmaceutically acceptable salt is citrate salt.

The terms "pharmaceutical composition," "liquid pharmaceutical composition," "pharmaceutical product," "pharmaceutical dosage form," "dosage form," "composition," "pharmaceutical formulation," etc., refer to a pharmaceutical composition administered to a human subject in need of treatment, which is typically in the form of solution, syrup, elixir, suspension, powder or granules for oral administration.

The terms "dosage", "dose unit" or "dose" as used herein means the amount of a pharmaceutical formulation comprising therapeutically active agent(s) administered at a time. "Dosage", "dose unit" or "dose" includes administration of one or more units of pharmaceutical formulation administered at the same time.

The term "solution" according to disclosure is a mixture of one or more substances dispersed molecularly (i.e., dissolved) in a dissolving liquid medium or vehicle. The solution is preferably homogeneous, in the sense that each active pharmaceutical ingredient is essentially uniformly distributed and concentrated in the solution. The liquid solution may be viscous (such as syrup) or not.

A "pharmaceutically acceptable vehicle" according to the invention is, without limitation: water, purified water, isopropyl alcohol, methanol, acetone, ethanol, 1-propanol, butanediol or combinations thereof.

An "aqueous solution" according to the disclosure is a solution that is at least 80% water by weight, preferably at least 90% water by weight, more preferably at least 95% water by weight and most preferably at least 98% water by weight. In certain embodiments, aqueous solutions of the present invention include solutions containing appropriate stabilizers, solubilizers, buffering agents, anti-oxidants, chelating agents, preservatives, sweetening agents, flavoring agents, coloring agents and other pharmaceutically acceptable additives. Alternately, aqueous solutions of the present invention can contain no such additives and can consist solely of tofacitinib, a stabilizer, and purified water.

The term "solubility" means solubility of tofacitinib or its pharmaceutically acceptable salts in aqueous media such as water, buffer, gastrointestinal simulated fluid, gastrointestinal fluid and the like.

The terms "stable" and "stability" mean that the evolution of the product with time and/or under specific environmental conditions (i.e., temperature, humidity, etc.) has no significant effects on its quality, safety and/or efficacy for a given time period. It can be measured through the formation of degradation products (impurities), variation of pH, appearance (precipitation), microbial growth, and/or color. The term "stable" indicates both chemical and physical stability.

The term "degradation product" in the present disclosure refers to an unwanted chemical or impurity (including, but not limited to known or unknown related substances) that can develop during the manufacturing, transportation, and storage of drug products and can affect the efficacy of pharmaceutical products. It can form in response to changes in oxygen, light, temperature, pH, and humidity, or due to inherent characteristics of active ingredient, such as their reaction with excipients or on contact with the packaging.

The term "in vivo" in general means in the living body of a plant or animal, whereas the term "in vitro" generally means outside the body and in an artificial environment.

A "reference formulation" according to the present disclosure is a formulation that is used for comparison. Preferably, the reference formulation may refer to immediate release tablet containing 5 mg or 10 mg of tofacitinib or extended-release tablet containing 11 mg or 22 mg of tofacitinib or oral solution containing 1 mg/mL of tofacitinib. Preferably, the reference formulation corresponds to an oral dosage form of tofacitinib, which is currently marketed under brand names Xeljanz® (tofacitinib immediate release tablet or oral solution) and Xeljanz® XR (tofacitinib extended release tablet).

The term "peak time of plasma drug concentration ($T_{max}$)" means the time when peak plasma drug concentration ($C_{max}$) is attained after drug administration.

The term "peak plasma drug concentration ($C_{max}$)" means the maximum plasma drug concentration attained after drug administration.

The term "$AUC_{0-infinity}$" means the area under a plasma drug concentration-time curve from time point of 0 to infinity after drug administration, and the term "$AUC_{0-t}$" means the area under a plasma drug concentration-time curve from time point of 0 to t after drug administration.

Pharmacokinetic parameters for the compositions can be measured in a single or multiple dose study using a replicate or a non-replicate design. For example, the pharmacokinetic parameters can be measured in a single dose pharmacokinetic study using a two-period, two-sequence crossover design. Alternately, a four-period, replicate design crossover study may also be used. Pharmacokinetic parameters characterizing rate and extent of tofacitinib absorption are evaluated statistically. The area under the plasma concentration-time curve from time zero to the time of measurement of the last quantifiable concentration ($AUC_{0-t}$) and to infinity ($AUC_{0-infinity}$), $C_{max}$, and $T_{max}$ can be determined according to standard techniques. Statistical analysis of pharmacokinetic data is performed on logarithmic transformed data (e.g., $AUC_{0-t}$, $AUC_{0-infinity}$, or $C_{max}$ data) using analysis of variance (ANOVA).

An embodiment of the disclosure is directed to stable liquid pharmaceutical compositions of tofacitinib or its pharmaceutically acceptable salt thereof, particularly wherein tofacitinib is present at a concentration of 1 mg/mL or more.

Another embodiment of the disclosure is directed to a pharmaceutical composition of the present application comprises tofacitinib or a pharmaceutically acceptable salt thereof, wherein tofacitinib concentration is about 1 mg/mL to about 10 mg/mL and preferably 1 mg/mL.

Preferably, the liquid pharmaceutical composition will be provided in a dosage form that is suitable for oral administration, including but not limited to a solution, syrup, or elixir. The pharmaceutical compositions may be formulated according to conventional pharmaceutical practice.

Generally, the present invention provides stable aqueous tofacitinib solutions at concentrations higher than the 0.2 mg/mL concentration, and methods of preparing such solutions. In particular, the present invention provides stable aqueous tofacitinib solutions for oral administration having concentrations about 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9 and 6.0 mg/mL.

An embodiment of the disclosure is directed to a pharmaceutical composition comprising tofacitinib or its pharmaceutically acceptable salts thereof and an anti-oxidant, wherein the composition further comprises additional pharmaceutically acceptable excipients. In another embodiment, the pharmaceutical composition of the present invention comprises tofacitinib and tartaric acid as anti-oxidant.

In one embodiment of the disclosure, the stable liquid compositions suitable for oral administration of the present invention comprises (a) tofacitinib at a concentration of 1 mg/mL; (b) purified water; and (c) one or more other pharmaceutically acceptable excipients, wherein the liquid composition is an aqueous solution, a syrup or an elixir.

Another embodiment covers stable liquid compositions suitable for oral administration comprising (a) tofacitinib at a concentration of 1 mg/mL; (b) purified water; and (c) one or more pharmaceutically acceptable excipients selected from the group consisting of stabilizers, solubilizers, pH adjusting agents, buffering agents, thickening agents, anti-oxidants, chelating agents, preservatives, flavoring agents, sweetening agents, coloring agents and mixtures thereof.

Another embodiment covers a method for treating and/or preventing an autoimmune disorder/disease in a human subject, comprising administering stable liquid compositions suitable for oral administration comprising (a) tofacitinib at a concentration of 1 mg/mL; (b) purified water; and (c) one or more pharmaceutically acceptable excipients selected from the group consisting of stabilizers, solubilizers, pH adjusting agents, buffering agents, thickening agents, anti-oxidants, chelating agents, preservatives, flavoring agents, sweetening agents, coloring agents and mixtures thereof.

In another embodiment, stable liquid pharmaceutical composition of tofacitinib suitable for oral administration comprises (a) tofacitinib at a concentration of about 1 mg/mL or more; (b) pharmaceutically acceptable liquid vehicle; and (c) at least one chelating agent and (d) one or more other pharmaceutically acceptable excipients.

In yet another embodiment, stable liquid pharmaceutical composition of tofacitinib suitable for oral administration comprises (a) tofacitinib at a concentration of about 1 mg/mL or more; (b) pharmaceutically acceptable liquid vehicle; and (c) at least one stabilizer; (d) at least one anti-oxidant and e) one or more other pharmaceutically acceptable excipients.

In yet another embodiment, stable liquid pharmaceutical composition of tofacitinib suitable for oral administration comprises (a) tofacitinib at a concentration of about 1 mg/mL or more; (b) pharmaceutically acceptable liquid vehicle; and (c) at least one anti-oxidant; (d) at least one chelating agent and e) one or more other pharmaceutically acceptable excipients.

In yet another embodiment, stable liquid pharmaceutical composition of tofacitinib suitable for oral administration comprises (a) tofacitinib at a concentration of about 1 mg/mL or more; (b) pharmaceutically acceptable liquid vehicle; and (c) at least one stabilizer; (d) at least one anti-oxidant; (e) at least one chelating agent and f) one or more other pharmaceutically acceptable excipients.

In yet another embodiment, stable liquid pharmaceutical composition of tofacitinib suitable for oral administration comprises (a) tofacitinib at a concentration of about 1 mg/mL or more; (b) pharmaceutically acceptable liquid vehicle; and (c) at least one anti-oxidant; (d) one or more other pharmaceutically acceptable excipients.

Another embodiment covers stable liquid compositions suitable for oral administration comprises (a) tofacitinib at a concentration of about 1 mg/mL or more; (b) pharmaceutically acceptable liquid vehicle; and (c) at least one anti-oxidant and d) one or more other pharmaceutically acceptable excipients, wherein the concentration of the anti-oxidant ranges from about 0.1 mg/mL to about 10 mg/mL, from about 0.3 mg/mL to about 5 mg/mL.

Yet another embodiment covers stable liquid compositions suitable for oral administration comprises (a) tofacitinib at a concentration of about 1 mg/mL or more; (b) pharmaceutically acceptable liquid vehicle; and (c) at least one anti-oxidant and (d) one or more other pharmaceutically acceptable excipients, wherein the weight ratio of anti-oxidant to tofacitinib is from about 0.1:1 to about 1:10, preferably about 1:3.

In an embodiment, stable liquid pharmaceutical compositions of tofacitinib suitable for oral administration comprises (a) tofacitinib at a concentration of about 1 mg/mL or more; (b) purified water (c) tartaric acid and (d) one or more other pharmaceutically acceptable excipients, wherein the weight ratio of anti-oxidant to tofacitinib is from about 0.1:1 to about 1:10, preferably about 1:3.

In one embodiment, pharmaceutical composition comprising tofacitinib can be formulated at any suitable pH. The pH of the pharmaceutical composition is preferably from about 4 to about 5, when measured at room temperature. In one embodiment, pharmaceutical composition comprising tofacitinib can be formulated by using any suitable pH adjusting agent.

In an embodiment, stable liquid compositions suitable for oral administration comprises (a) tofacitinib at a concentration of about 1 mg/mL or more; (b) pharmaceutically acceptable liquid vehicle; and (c) at least one anti-oxidant and (d) one or more other pharmaceutically acceptable excipients, wherein the composition has a pH in the range of about 4 to about 5.

In an embodiment, stable liquid pharmaceutical compositions of tofacitinib suitable for oral administration comprises (a) tofacitinib at a concentration of about 1 mg/mL or more; (b) purified water; (c) tartaric acid and (d) one or more other pharmaceutically acceptable excipients, wherein pH of pharmaceutical composition ranges from about 4 to about 5.

In an embodiment, stable liquid pharmaceutical compositions of tofacitinib suitable for oral administration comprises (a) 1 mg/mL tofacitinib (b) 0.5 mg/mL tartaric acid (c) purified water and (d) one or more other pharmaceutically acceptable excipients, wherein pH of pharmaceutical composition ranges from about 4 to about 5.

In an embodiment, stable liquid pharmaceutical compositions of tofacitinib suitable for oral administration comprises (a) 1 mg/mL tofacitinib (b) 0.5 mg/mL tartaric acid (c) purified water and (d) one or more other pharmaceutically acceptable excipients, wherein the pH of pharmaceutical composition ranges from about 4 to about 4.6.

In an embodiment, stable liquid pharmaceutical compositions of tofacitinib suitable for oral administration comprises (a) 1 mg/mL tofacitinib (b) 0.5 mg/mL tartaric acid (c) purified water and (d) one or more other pharmaceutically acceptable excipients, wherein the pH of pharmaceutical composition ranges from about 4 to about 4.6, wherein the pharmaceutical composition is stable for at least 6 months at 40° C./75% RH.

In an embodiment, stable liquid pharmaceutical compositions of tofacitinib suitable for oral administration comprises (a) 1 mg/mL tofacitinib (b) 0.5 mg/mL tartaric acid (c) purified water and (d) one or more other pharmaceutically acceptable excipients, wherein the pH of pharmaceutical composition ranges from about 4 to about 4.6, wherein the level of total impurities in the composition is less than about 3% w/w as measured by HPLC, when stored at 40° C./75% RH for at least a period of 6 months.

In an embodiment, stable liquid compositions suitable for oral administration comprises (a) tofacitinib at a concentration of about 1 mg/mL or more; (b) pharmaceutically acceptable liquid vehicle; (c) at least one anti-oxidant and (d) one or more other pharmaceutically acceptable excipients, wherein the composition is stable for at least 6 months at 40° C./75% RH.

In an embodiment, stable liquid compositions suitable for oral administration comprises (a) tofacitinib at a concentration of about 1 mg/mL or more; (b) purified water; (c) tartaric acid and (d) one or more other pharmaceutically acceptable excipients, wherein the composition is stable for at least 6 months at 40° C./75% RH.

In yet another embodiment, stable liquid composition of tofacitinib suitable for oral administration comprises (a) tofacitinib at a concentration of about 1 mg/mL or more; (b) one pharmaceutically acceptable liquid vehicle; and (c) at least one anti-oxidant and (d) one or more other pharmaceutically acceptable excipients, wherein the composition is stable for at least 6 months at 25° C./60% RH.

In yet another embodiment, stable liquid composition of tofacitinib suitable for oral administration comprises (a) tofacitinib at a concentration of about 1 mg/mL or more; (b) purified water; (c) tartaric acid and (d) one or more other pharmaceutically acceptable excipients, wherein the composition is stable for at least 6 months at 25° C./60% RH.

In yet another embodiment, stable liquid composition suitable for oral administration comprises (a) tofacitinib at a concentration of about 1 mg/mL or more; (b) pharmaceutically acceptable liquid vehicle; and (c) at least one anti-oxidant and (d) one or more other pharmaceutically acceptable excipients, wherein the composition is stable for at least 12 months at 25° C./60% RH.

In yet another embodiment, stable liquid composition suitable for oral administration comprises (a) tofacitinib at a concentration of about 1 mg/mL or more; (b) purified water; (c) tartaric acid and (d) one or more other pharmaceutically acceptable excipients, wherein the composition is stable for at least 12 months at 25° C./60% RH.

In an embodiment, stable liquid composition suitable for oral administration comprises (a) tofacitinib at a concentration of about 1 mg/mL or more; (b) pharmaceutically acceptable liquid vehicle; and (c) at least one anti-oxidant and (d) one or more other pharmaceutically acceptable excipients, wherein the level of total impurities in the composition is less than about 3% w/w, preferably less than about 2% w/w, preferably less than about 1.5% w/w, more preferably less than about 1% w/w, more preferably less than about 0.5% w/w as measured by HPLC.

In an embodiment, stable liquid composition suitable for oral administration comprises (a) tofacitinib at a concentration of about 1 mg/mL or more; (b) pharmaceutically acceptable liquid vehicle; and (c) at least one anti-oxidant and (d) one or more other pharmaceutically acceptable excipients, wherein the level of total impurities in the composition is less than about 3% w/w, preferably less than about 2% w/w, preferably less than about 1.5% w/w, more preferably less than about 1% w/w, more preferably less than about 0.5% w/w as measured by HPLC, when stored at 25° C./60% RH or 40° C./75% RH for at least a period of 6 months.

In an embodiment, stable liquid composition suitable for oral administration comprises (a) tofacitinib at a concentration of about 1 mg/mL or more; (b) pharmaceutically acceptable liquid vehicle; and (c) at least one anti-oxidant and (d) one or more other pharmaceutically acceptable excipients, wherein the level of total impurities in the composition is less than about 3% w/w, preferably less than about 2% w/w, preferably less than about 1.5% w/w, more preferably less than about 1% w/w, more preferably less than about 0.5% w/w as measured by HPLC, when stored at 25° C./60% RH or 40° C./75% RH for at least a period of 12 months.

In an embodiment, stable liquid composition suitable for oral administration comprises (a) tofacitinib at a concentration of about 1 mg/mL or more; (b) purified water; and (c) tartaric acid and (d) one or more other pharmaceutically acceptable excipients, wherein the level of total impurities in the composition is less than about 3% w/w, preferably less than about 2% w/w, preferably less than about 1.5% w/w, more preferably less than about 1% w/w, more preferably less than about 0.5% w/w as measured by HPLC, when stored at 25° C./60% RH or 40° C./75% RH for at least a period of 6 months.

In an embodiment, one or more pharmaceutically acceptable excipients combined with tofacitinib comprises stabilizer, solubilizer, sweetening agent, flavouring agent, preservative, anti-oxidants, chelating agent, viscosity modifier, pH adjusting agent, buffering agent, coloring agent and combinations thereof.

In embodiments, the stabilizer can be selected from polyvinylpyrrolidone, cyclodextrin or a cyclodextrin derivative. In embodiments, concentration of stabilizer in the composition ranges from about 10% to about 60% w/v of total composition.

In another embodiment, pharmaceutical composition of the present application comprises tofacitinib and a cyclodextrin derivative, wherein cyclodextrin derivative concentration is about 10 mg/mL to about 400 mg/mL, preferably from about 20 mg/mL to about 80 mg/mL, more preferably about 25 mg/mL.

The term "cyclodextrin" refers to cyclic oligosaccharides consisting of ($\alpha$-1,4)-linked $\alpha$-D-glucopyranose units. Each subunit of a naturally-occurring (unmodified or parent)

cyclodextrin has secondary hydroxy groups at the 2- and 3-positions and a primary hydroxy group at the 6-position. A cyclodextrin may be thought of as a toroid or hollow truncated cone, which because of the location of the hydroxy groups has a hydrophilic exterior surface and a comparatively less lipophilic internal cavity. The internal cavity may capture at least a portion of a drug molecule, such as tofacitinib, which results in the formation of an inclusion complex. Covalent bonds are neither made nor broken during the formation of the drug-cyclodextrin complex. In aqueous solution, the complex dissociates, resulting in free drug molecules in equilibrium with drug molecules bound in the cyclodextrin cavities.

In one embodiment, the cyclodextrin of the present application includes α-cyclodextrin, β-cyclodextrin, δ-cyclodextrin, γ-cyclodextrin, or combinations thereof. In an embodiment, the cyclodextrin of the present application preferably includes either a substituted or non-substituted β-cyclodextrin.

Substituted cyclodextrins increase the solubility of the cyclodextrin and mitigate toxic effects associated with unsubstituted cyclodextrins. Examples of substituted cyclodextrins include hydroxypropyl-β-cyclodextrin (HP-β-CD) and sulfobutylether-β-cyclodextrin (SBE-β-CD), Cavasol® W7 HP (hydroxypropyl-β-cyclodextrin (HP-β-CD), Kleptose® HP (hydroxypropyl-β-cyclodextrin (HP-β-CD)), Cavamax® W7 (β-cyclodextrin), Captisol® (sulfoalkyl ether-β-cyclodextrin), Cavasol® W7 M (methyl-β-cyclodextrin), Cavasol® W8 HP (hydroxypropyl-γ-cyclodextrin), Cavamax® W8 (γ-cyclodextrin), Cavamax® W6 (α-cyclodextrin).

In an embodiment, pharmaceutical compositions comprising tofacitinib can be formulated at any suitable pH using pH adjusting agent and to maintain pH of the said composition using suitable buffering agent.

In an embodiment, suitable pH adjusting agent include acetic acid, ammonia solution, strong; acetic acid, glacial; ammonium carbonate; anhydrous; diethanolamine; potassium hydroxide; fumaric acid; sodium bicarbonate; hydrochloric acid; sodium borate; hydrochloric acid, diluted; sodium carbonate; malic acid; trolamine; phosphoric acid; sodium hydroxide; nitric acid; phosphoric acid, diluted; propionic acid; sulfuric acid.

In an embodiment, suitable buffering agents include acetic acid; adipic acid; ammonium carbonate; ammonium phosphate; boric acid; lactic acid; phosphoric acid; potassium citrate; potassium metaphosphate; potassium phosphate, dibasic; potassium phosphate, monobasic; sodium acetate; sodium citrate; sodium lactate solution; sodium phosphate, dibasic; sodium phosphate, monobasic; succinic acid.

In an embodiment, suitable sweetening agents include aspartame, saccharin, sucralose, acesulfame potassium and the like.

In an embodiment, suitable flavoring agents include cherry flavor, artificial banana flavor, caramel, chocolate mint flavor, grape flavor, wild cherry flavor, maltitol, raspberry flavor, strawberry flavor, mixed berry flavor, citrus flavor, orange flavor, pineapple flavor, citrus lime flavor, citrus cream flavor, cherry vanilla flavor, cranberry flavor, creme de menthe flavor and mixtures thereof.

In embodiments, the solubilizer can be selected from but not limited to, for example, propylene glycol, polyethylene glycol, glycerol, Tween 20, Tween 80, sodium lauryl sulfate (SLS) or combinations thereof.

A "chelating agent" according to the disclosure is an agent which forms via two or more of its functional groups stable complexes with metal cations, e.g., preferably a polyacetic acid or a pharmaceutically acceptable salt thereof like disodium EDTA and DTPA. Chelating agents are capable of forming more than one bond. Ethylene diamine, for example, is bidentate (two links), tripyridyl is tridentate (three) and disodium ethylene diamine tetra acetic acid (disodium EDTA) is hexadentate (six) which makes it particularly effective as a pharmaceutical chelating agent. One of the consequences of chelation typically is the formation of a cyclic structure, which may have high thermodynamic and thermal stability.

Preferably the chelating agent is a bivalent cation chelator and more preferably, the chelator is selected from the group consisting of disodium ethylenediaminetetraacetic acid (disodium EDTA), diethylenetriaminepentaacetic acid (DTPA), ethylene glycol-bis (β-aminoethyl ether)-tetra acetic acid (EGTA), N-(hydroxyethyl) ethylenediaminetriacetic acid (HEDTA), nitrilotriacetic acid (NTA), triethanolamine, 8-hydroxyquinoline, phosphoric acid, gluconic acid, saccharic acid, thiodipropionic acid, acetonic dicarboxylic acid, lecithin, di(hydroxyethyl)glycine, phenylalanine, tryptophan, glycerine, sorbitol and pharmaceutically acceptable salts thereof. More preferably, the chelating agent is selected from the group consisting of disodium EDTA, DTPA, phosphoric acid, gluconic acid or a pharmaceutically acceptable salt thereof. The amount of chelating agent may range from about 0.1 mg/mL to about 1 mg/mL of the composition.

An "anti-oxidant" according to the disclosure is an agent which inhibits oxidation and thus is used to prevent the deterioration of preparations by the oxidative process. Such compounds include by way of example and without limitation, acetone, sodium bisulfate, ascorbic acid, ascorbyl palmitate, citric acid, tartaric acid, glycine, L-cysteine hydrochloride, L-methionine, butylated hydroxy anisole (BHA), butylated hydroxytoluene (BHT), hydro phosphorous acid, monothioglycerol, propyl gallate, sodium ascorbate, sodium citrate anhydrous, sodium citrate dihydrate, sodium sulfide, sodium sulfite, sodium bisulfite, sodium formaldehyde sulfoxylate, thioglycolic acid, sodium metabisulfite and others known to those of ordinary skill in the art. The amount of anti-oxidant may range from about 0.1 mg/mL to about 50 mg/mL of the composition.

In an embodiment of the disclosure, the anti-oxidant concentration ranges from about 0.01% to about 50% w/w of total composition, preferably 0.05% w/w of total composition.

In an embodiment of the disclosure, the anti-oxidant concentration ranges from about 0.01 mg/mL to about 50 mg/mL of total composition, preferably 0.5 mg/mL of total composition.

A suitable viscosity modifier according to the disclosure is cellulose or cellulose derivatives such as ethylcellulose, hydroxyethylcellulose, hydroxypropylcellulose, caboxymethylcellulose, sodium hydroxypropyl methylcellulose, hypromellose, methylcellulose, methylethylcellulose, sodium carboxymethylcellulose, Aerosil (silicon dioxide), cetostearyl alcohol, cetyl alcohol, stearyl alcohol, Gelucires 33/01, 39/01 and 43/01, stearyl alcohol carbomer, xanthan gum, maltodextrin, acacia, tragacanth, povidone and polyvinyl alcohol and mixtures thereof.

In an embodiment of the disclosure, exemplary preservatives include benzyl alcohol, xylitol, erythorbic acid, fumaric acid, malic acid, propyl gallate, sodium benzoate, parabens (methyl-, ethyl-, butyl-), benzoic acid, potassium sorbate, and vanillin.

Any appropriate form of tofacitinib can be used to prepare oral solutions of the present invention. For example, any crystalline or amorphous form of tofacitinib may be used in the pharmaceutical composition of the present application. In a preferred embodiment, appropriate forms of tofacitinib include powdered, lyophilized, spray-dried, hot-melt extruded or micro-fluidized tofacitinib. In other embodiments, the tofacitinib can be provided as an aqueous or non-aqueous solution of tofacitinib, including buffered solutions.

The pharmaceutical compositions of present application may be filled into any suitable pharmaceutically acceptable containers. For example, the pharmaceutically acceptable container may be selected from group consisting of bottles and syringes. The bottle can be made of any material convenient with the storage and the use requirements comprising polymers, metal and glass and so on. It is of importance that the bottle material does not interfere with the components of the liquid formulation as disclosed herein. In an embodiment of the disclosure, the pharmaceutically acceptable container is made of glass. In order to protect the active ingredients from light-induced degradation, a preferred embodiment comprises amber glass bottle.

The bottle capacity can be adapted to the volume to be administrated for the period during which the liquid formulation as disclosed herein is stable. For instance, a solution which is stable for 60 days after opening associated to an administration of two doses of 5 mL or weight-based equivalent twice per day may be stored into bottle of about 240 mL. The one skilled in the art will easily adapt the volume of the bottle to that needed as previously suggested.

The syringe is made of glass, plastic or any material convenient with the use and the storage of the liquid solutions as disclosed herein. The syringe may be graduated to facilitate the administration of the liquid solution. In an embodiment, the syringe has 3.2 mL, 4 mL, and 5 mL gradations.

The cap (or closure) is any article for closing a suitably shaped opening. It encompasses, but is not limited to, childproof closures, waterproof closures, pipette-associated caps, solid caps, plastic or polymeric caps. In an embodiment, the cap is screwed on the bottle top or interlocked with the top of the bottle.

A sealing element may be required for the tightness of the system bottle-cap or bottle-pipette-cap or bottle-pipette or pipette-cap. This element can be supplied on its own and further fit in the bottle-neck, or around the pipette, or in the cap, or it can be previously adapted to the bottle, the cap or the pipette.

The invention also relates to a kit of parts comprising a package containing bottles of the liquid formulation as disclosed herein and syringe intended to remove the needed amount of the liquid formulation and/or instructions.

In yet another embodiment, the invention relates to a kit comprising a) a liquid dosage form comprising therapeutically effective amount of tofacitinib; and b) instructions for oral administration of the dosage form.

In another embodiment, the invention relates to a kit of parts allowing the extemporaneously preparation of the solutions according to the invention.

In an embodiment, the pharmaceutically acceptable container may be a bottle, wherein the bottle was selected from group consisting of a glass bottle and a plastic bottle. Examples of glass bottle include, but are not limited to Type I, II and III borosilicate glass bottles. In an embodiment, the pharmaceutically acceptable container was a glass bottle, wherein the glass bottle may be amber color glass bottle or clear glass bottle.

Examples of plastic bottles include, but are not limited to, high-density polyethylene (HDPE), polyethylene terephthalate (PET) and polypropylene (PP) bottles. In an embodiment, the pharmaceutically acceptable container is a plastic bottle, wherein the plastic bottle may be amber color, white opaque or translucent plastic bottle. In preferred embodiment, the HDPE bottles will be available in 30, 60, 120, 240, 250, 418-mL & 500-mL fill volumes.

In an embodiment, the pharmaceutical composition of present application is packed in a kit comprising bottle with child resistant cap, dosing syringe, adapter and dosing syringe.

Stability. Certain embodiments relate to pharmaceutical compositions as described herein, which are stable, e.g., stable over the shelf life of the drug product. In certain aspects, the term "stable" is defined as no more than about 5% loss of tofacitinib under typical commercial storage conditions. In certain embodiments, the formulations of the present invention will have no more than about 3% loss of tofacitinib, more preferably, no more than about 2% loss of tofacitinib, under typical commercial storage conditions. The composition retains at least about 95% of the potency of tofacitinib after storing the composition at 40° C. and 75% relative humidity for at least six months. In certain aspects, the term "stable" refers to chemical stability. The formulation according to the disclosure is considered stable when not more than 0.5% w/w of each impurity is formed on storage at 40° C. and 75% relative humidity or at 25° C. and 60% relative humidity for a period of at least six months. In certain aspects, the term "stable" refers to chemical stability, wherein not more than 3% w/w of total impurities formed on storage at 40° C. and 75% relative humidity or at 25° C. and 60% relative humidity for a period of at least six months.

In an embodiment of the disclosure, stable liquid composition suitable for oral administration comprises (a) tofacitinib at a concentration of about 1 mg/mL or more; (b) pharmaceutically acceptable liquid vehicle; and (c) at least one anti-oxidant and (d) one or more other pharmaceutically acceptable excipients, wherein the composition is stable for at least 12 months at 25° C./60% RH.

Stability according to the invention is determined by monitoring certain impurities. In particular, Pyrrolo Pyrimidine impurity, Impurity-A, Impurity-B, Amino Pyrimidine Impurity, N-Oxide Impurity, Ethyl Ester Impurity and 1-Amide impurity are monitored. The structures of these impurities are shown below:

| Impurity Name | IUPAC name | Chemical structure |
|---|---|---|
| Amino Pyrimidine impurity | 3-{(3R,4R)-3-[(6-aminopyrimidin-4-yl)(methyl)amino]-4-methylpiperidin-1-yl}-3-oxopropanenitrile impurity | 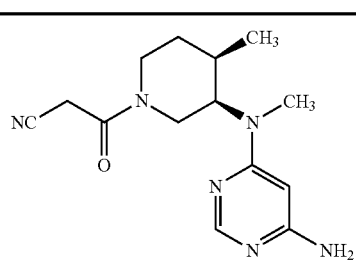 |

-continued

| Impurity Name | IUPAC name | Chemical structure |
|---|---|---|
| Impurity-B | N-methyl-N-[(3R,4R)-4-methylpiperidin-3-yl]-7H-pyrrolo[2,3-d]pyrimidin-4-amine hydrochloride | 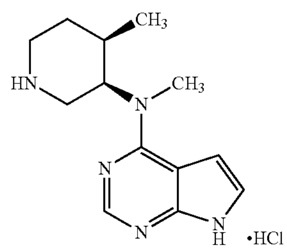 [SMILES: C[C@@H]1CCNC[C@@H]1N(C)c1ncnc2[nH]ccc12 ; Cl] |
| Pyrrolo Pyrimidine impurity | 3-{(3R,4R)-3-[6,7-dihydro-5Hpyrrolo[2,3-d]pyrimidin-4-yl(methyl)amino]-4-methylpiperidin-1-yl}-3-oxo-propanenitrile | 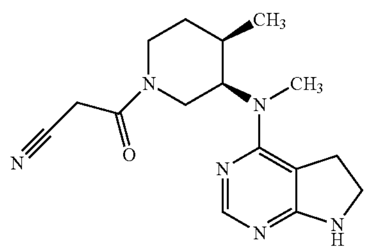 [SMILES: C[C@@H]1CCN(C(=O)CC#N)C[C@@H]1N(C)c1ncnc2c1CCN2] |
| 1-Amide impurity or Impurity-L | (3R,4R)-4-Methyl-3-(methyl-7H-pyrrolo[2,3-d]pyrimidin-4-ylamino)-β-oxo-1-piperidinepropanamide | 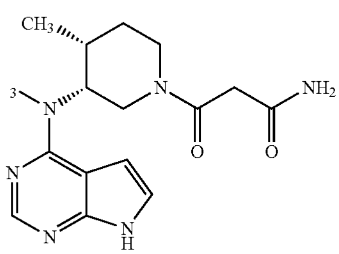 |
| N-Oxide impurity | (3R,4R)-4-Methyl-3-(methyloxido-7H-pyrrolo[2,3-d]pyrimidin-4-ylamino)-β-oxo-1-piperidinepropanenitrile | 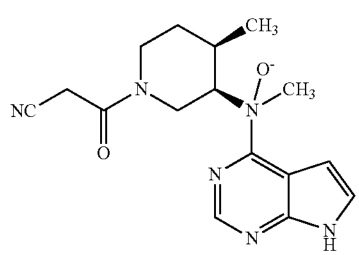 |
| Impurity-A | 3-{(3R,4R)-3-[(2-chloro-7H-pyrrolo[2,3-d]pyrimidin-4-yl)(methyl)amino]-4-methylpiperidin-1-yl}-3-oxopropanenitrile | 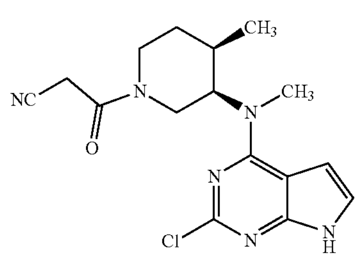 [SMILES: C[C@@H]1CCN(C(=O)CC#N)C[C@@H]1N(C)c1nc(Cl)nc2[nH]ccc12] |
| Ethyl ester impurity | Ethyl 3-{(3R,4R)-4-methyl-3-[methyl(7H-pyrrolo[2,3-d]pyrimidin-4-yl)amino]piperidin-1-yl}-3-oxoprop | 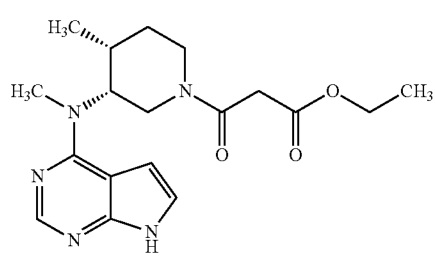 [SMILES: CCOC(=O)CC(=O)N1CC[C@@H](C)[C@@H](N(C)c2ncnc3[nH]ccc23)C1] |

Impurity B is formed when tofacitinib undergoes an acid-base hydrolysis. The acid-base hydrolysis occurs at a pH of below 4 in aqueous solution. It was found that the amount of impurity B observed was above ICH identification limit of "0.5% known impurity under accelrated conditions."

Surprisingly, it was found that when the composition was prepared in a pH range from about 4 to about 5, the percentage content of impurity B was no more than the 0.5% limit. Thus, the present disclosure provides a liquid pharmaceutical composition of tofacitinib with pH range from about 4 to about 5, wherein the level of Impurity-B in the composition is less than about 0.5% w/w as measured by HPLC, when stored at 25° C./60% RH or 40° C./75% RH for at least a period of 6 months.

In an embodiment, stable liquid pharmaceutical compositions of tofacitinib suitable for oral administration comprises (a) tofacitinib at a concentration of about 1 mg/mL or more; (b) a pharmaceutically acceptable liquid vehicle and (c) optionally, one or more other pharmaceutically acceptable excipients, wherein the pH of pharmaceutical composition ranges from about 4 to about 5, wherein the level of Impurity-B in the composition is less than about 0.5% w/w as measured by HPLC, when stored at 25° C./60% RH or 40° C./75% RH for at least a period of 6 months.

In an embodiment, stable liquid pharmaceutical compositions of tofacitinib suitable for oral administration comprises (a) tofacitinib at a concentration of about 1 mg/mL or more; (b) pharmaceutically acceptable liquid vehicle and (c) optionally one or more other pharmaceutically acceptable excipients, wherein the pH of pharmaceutical composition ranges from about 4 to about 4.6, wherein the level of Impurity-B in the composition is less than about 0.5% w/w as measured by HPLC, when stored at 25° C./60% RH or 40° C./75% RH for a period of at least 6 months.

In an embodiment, stable liquid pharmaceutical compositions of tofacitinib suitable for oral administration comprises (a) tofacitinib at a concentration of about 1 mg/mL or more; (b) a pharmaceutically acceptable liquid vehicle and (c) at least an anti-oxidant (d) optionally one or more other pharmaceutically acceptable excipients, wherein the pH of pharmaceutical composition ranges from about 4 to about 4.6, wherein the level of Impurity-B in the composition is less than about 0.5% w/w as measured by HPLC, when stored at 25° C./60% RH or 40° C./75% RH for a period of at least 6 months.

In an embodiment, stable liquid pharmaceutical compositions of tofacitinib suitable for oral administration comprises (a) tofacitinib at a concentration of about 1 mg/mL or more; (b) purified water and (c) optionally one or more other pharmaceutically acceptable excipients, wherein the pH of pharmaceutical composition ranges from about 4 to about 4.6, wherein the level of Impurity-B in the composition is less than about 0.5% w/w as measured by HPLC, when stored at 25° C./60% RH or 40° C./75% RH for a period of at least 6 months.

In an embodiment, stable liquid pharmaceutical compositions of tofacitinib suitable for oral administration comprises (a) tofacitinib at a concentration of about 1 mg/mL or more; (b) purified water (c) tartaric acid and (d) optionally one or more other pharmaceutically acceptable excipients, wherein the pH of pharmaceutical composition ranges from about 4 to about 4.6, wherein the level of Impurity-B in the composition is less than about 0.5% w/w as measured by HPLC, when stored at 25° C./60% RH or 40° C./75% RH for a period of at least 6 months.

It was found that variations in pH over 4.6 resulted in precipitation of tofacitinib. For example, at a pH of over 4.6, tofacitinib precipitates out in aqueous solutions under storage conditions of 25° C./60% RH for a period of at least 6 months. Such precipitation is undesirable as it renders the composition non-compliant with the standard assay specification. Such a non-compliance is often indicative of the composition's lack of prolonged shelf life.

Surprisingly, it was found that a composition with pH below 4.8 did not result stability issues arising from tofacitinib precipitation. The present disclosure provides a liquid pharmaceutical composition of tofacitinib with pH range from about 3.7 to about 4.6, was found to be free from precipitation, when stored at 25° C./60% RH for at least a period of 6 months.

The present disclosure provides a stable liquid pharmaceutical compositions of tofacitinib suitable for oral administration comprises (a) tofacitinib at a concentration of about 1 mg/mL or more; (b) a pharmaceutically acceptable liquid vehicle; and (c) optionally, one or more other pharmaceutically acceptable excipients, wherein the pH of pharmaceutical composition is not more than 4.6, wherein liquid pharmaceutical composition is free from precipitation, when stored at 25° C./60% RH for at least a period of 6 months.

In an embodiment, stable liquid pharmaceutical compositions of tofacitinib suitable for oral administration comprises (a) tofacitinib at a concentration of about 1 mg/mL or more; (b) a pharmaceutically acceptable liquid vehicle; and (c) optionally, one or more other pharmaceutically acceptable excipients, wherein the pH of pharmaceutical composition range from about 3.7 to about 4.6, wherein liquid pharmaceutical composition is free from precipitation, when stored at 25° C./60% RH for at least a period of 6 months.

In an embodiment, stable liquid pharmaceutical compositions of tofacitinib suitable for oral administration comprises (a) tofacitinib at a concentration of about 1 mg/mL or more; (b) a pharmaceutically acceptable liquid vehicle (c) at least one anti-oxidant and (d) optionally, one or more other pharmaceutically acceptable excipients, wherein the pH of pharmaceutical composition range from about 3.7 to about 4.6, wherein liquid pharmaceutical composition is free from precipitation, when stored at 25° C./60% RH for at least a period of 6 months.

In an embodiment, stable liquid pharmaceutical compositions of tofacitinib suitable for oral administration comprises (a) tofacitinib at a concentration of about 1 mg/mL or more; (b) purified water (c) tartaric acid and (d) optionally one or more other pharmaceutically acceptable excipients, wherein the pH of pharmaceutical composition ranges from about 3.7 to about 4.6, wherein liquid pharmaceutical composition is free from precipitation, when stored at 25° C./60% RH for at least a period of 6 months.

In yet another embodiment, stable liquid pharmaceutical composition of tofacitinib suitable for oral administration comprises (a) tofacitinib at a concentration of about 1 mg/mL or more; (b) pharmaceutically acceptable liquid vehicle; and (c) at least one anti-oxidant and (d) one or more other pharmaceutically acceptable excipients, wherein the pharmaceutical composition is stable for at least 6 months at 40° C./75% RH.

In yet another embodiment, stable liquid pharmaceutical composition of tofacitinib suitable for oral administration comprises (a) tofacitinib at a concentration of about 1 mg/mL or more; (b) purified water; (c) tartaric acid and (d) one or more other pharmaceutically acceptable excipients, wherein the pharmaceutical composition is stable for at least 6 months at 40° C./75% RH.

In yet another embodiment, stable liquid pharmaceutical composition of tofacitinib suitable for oral administration comprises (a) tofacitinib at a concentration of about 1 mg/mL or more; (b) pharmaceutically acceptable liquid vehicle; and (c) at least one anti-oxidant and (d) one or more other pharmaceutically acceptable excipients, wherein the pharmaceutical composition is stable for at least 6 months at 25° C./60% RH.

In yet another embodiment, stable liquid pharmaceutical composition of tofacitinib suitable for oral administration comprises (a) tofacitinib at a concentration of about 1 mg/mL or more; (b) purified water (c) tartaric acid and (d) one or more other pharmaceutically acceptable excipients, wherein the pharmaceutical composition is stable for at least 6 months at 25° C./60% RH.

In yet another embodiment, stable liquid pharmaceutical composition of tofacitinib suitable for oral administration comprises (a) tofacitinib at a concentration of about 1 mg/mL or more; (b) pharmaceutically acceptable liquid vehicle; and (c) at least one anti-oxidant and (d) one or more other pharmaceutically acceptable excipients, wherein the pharmaceutical composition is stable for at least 12 months at 40° C./75% RH.

In yet another embodiment, stable liquid pharmaceutical composition of tofacitinib suitable for oral administration comprises (a) tofacitinib at a concentration of about 1 mg/mL or more; (b) purified water; (c) tartaric acid and (d) one or more other pharmaceutically acceptable excipients, wherein the pharmaceutical composition is stable for at least 12 months at 40° C./75% RH.

In yet another embodiment, stable liquid pharmaceutical composition of tofacitinib suitable for oral administration comprises (a) tofacitinib at a concentration of about 1 mg/mL or more; (b) pharmaceutically acceptable liquid vehicle; and (c) at least one anti-oxidant and (d) one or more other pharmaceutically acceptable excipients, wherein the pharmaceutical composition is stable for at least 12 months at 25° C./60% RH.

In yet another embodiment, stable liquid pharmaceutical composition of tofacitinib suitable for oral administration comprises (a) tofacitinib at a concentration of about 1 mg/mL or more; (b) purified water; (c) tartaric acid and (d) one or more other pharmaceutically acceptable excipients, wherein the pharmaceutical composition is stable for at least 12 months at 25° C./60% RH.

In an embodiment, stable liquid pharmaceutical composition of tofacitinib suitable for oral administration comprises (a) tofacitinib at a concentration of about 1 mg/mL or more; (b) at least one pharmaceutically acceptable liquid vehicle; and (c) at least one anti-oxidant and (d) one or more other pharmaceutically acceptable excipients, wherein the level of total impurities in the composition is less than about 3% w/w, preferably less than about 2% w/w, preferably less than about 1.5% w/w, more preferably less than about 1% w/w, more preferably less than about 0.5% w/w as measured by HPLC.

In an embodiment, stable liquid pharmaceutical composition of tofacitinib suitable for oral administration comprises (a) tofacitinib at a concentration of about 1 mg/mL or more; (b) purified water; and (c) tartaric acid and (d) one or more other pharmaceutically acceptable excipients, wherein the level of total impurities in the composition is less than about 3% w/w, preferably less than about 2% w/w, preferably less than about 1.5% w/w, more preferably less than about 1% w/w, more preferably less than about 0.5% w/w as measured by HPLC.

In an embodiment, a stable liquid pharmaceutical composition of tofacitinib suitable for oral administration comprising: (a) tofacitinib at a concentration of about 1 mg/mL or more; (b) a pharmaceutically acceptable liquid vehicle; (c) one or more other pharmaceutically acceptable excipients, wherein the pH of pharmaceutical composition ranges from about 2.5 to about 7.5.

In an embodiment, stable liquid pharmaceutical compositions of tofacitinib suitable for oral administration comprises (a) tofacitinib at a concentration of about 1 mg/mL or more; (b) pharmaceutically acceptable liquid vehicle; and (c) at least one anti-oxidant and (d) one or more other pharmaceutically acceptable excipients, wherein pH of pharmaceutical composition ranges from about 2.5 to about 7.5, preferably from about 3.5 to about 5.5, preferably from about 4 to about 5, wherein the level of total impurities in the composition is less than about 3% w/w, preferably less than about 2% w/w, preferably less than about 1.5% w/w, more preferably less than about 1% w/w, more preferably less than about 0.5% w/w as measured by HPLC.

In an embodiment, stable liquid pharmaceutical compositions of tofacitinib suitable for oral administration comprises (a) tofacitinib at a concentration of about 1 mg/mL or more; (b) purified water (c) tartaric acid and (d) one or more other pharmaceutically acceptable excipients, wherein pH of pharmaceutical composition ranges from about 2.5 to about 7.5, preferably from about 3.5 to about 5.5, preferably from about 4 to about 5, wherein the level of total impurities in the composition is less than about 3% w/w, preferably less than about 2% w/w, preferably less than about 1.5% w/w, more preferably less than about 1% w/w, more preferably less than about 0.5% w/w as measured by HPLC.

In an embodiment, stable liquid pharmaceutical compositions of tofacitinib suitable for oral administration comprises (a) tofacitinib at a concentration of about 1 mg/mL or more; (b) purified water (c) tartaric acid and (d) one or more other pharmaceutically acceptable excipients, wherein pH of pharmaceutical composition ranges from about 4 to about 5, wherein the level of total impurities in the composition is less than about 3% w/w as measured by HPLC.

In an embodiment, stable liquid pharmaceutical compositions of tofacitinib suitable for oral administration comprises (a) tofacitinib at a concentration of about 1 mg/mL or more; (b) purified water (c) 0.5 mg/mL tartaric acid and (d) one or more other pharmaceutically acceptable excipients, wherein pH of pharmaceutical composition ranges from about 4 to about 4.6, wherein the level of total impurities in the composition is less than about 3% w/w as measured by HPLC.

In an embodiment, stable liquid pharmaceutical compositions of tofacitinib suitable for oral administration comprises (a) tofacitinib at a concentration of about 1 mg/mL or more; (b) purified water (c) 0.05% w/w anti-oxidant and (d) one or more other pharmaceutically acceptable excipients, wherein pH of pharmaceutical composition ranges from about 4 to about 4.6, wherein the level of total impurities in the composition is less than about 3% w/w as measured by HPLC.

In an embodiment, stable liquid pharmaceutical compositions of tofacitinib suitable for oral administration comprises (a) tofacitinib at a concentration of about 1 mg/mL or more; (b) purified water (c) 0.05% w/w tartaric acid and (d) one or more other pharmaceutically acceptable excipients, wherein pH of pharmaceutical composition ranges from about 4 to about 4.6, wherein the level of total impurities in the composition is less than about 3% w/w as measured by HPLC.

Dosage and Administration. The dose of the therapeutic compound will be in the range from about 0.1 to about 50 mg/mL per recipient per day. Exemplary doses of therapeutic compound range from 0.1 mg/mL to 50 mg/mL, including dosages of 0.1 mg/mL, 0.2 mg/mL, 0.3 mg/mL, 0.4 mg/mL, 0.5 mg/mL, 0.6 mg/mL, 0.7 mg/mL, 0.8 mg/mL, 0.9 mg/mL, 1 mg/mL, 2 mg/mL, 3 mg/mL, 4 mg/mL, 5 mg/mL, 6 mg/mL, 7 mg/mL, 8 mg/mL, 9 mg/mL, 10 mg/mL, 11 mg/mL, 12 mg/mL, 13 mg/mL, 14 mg/mL, 15 mg/mL, 16 mg/mL, 17 mg/mL, 18 mg/mL, 19 mg/mL, 20 mg/mL, 21 mg/mL, 22 mg/mL, 25 mg/mL, 30 mg/mL, 35 mg/mL, 40 mg/mL, 45 mg/mL, 50 mg/mL. The effective dosage range of the pharmaceutically acceptable salts may be calculated based on the weight of the active moiety to be delivered. If the salt exhibits activity itself, the effective dosage may be estimated as above using the weight of the salt, or by other means known to those skilled in the art.

As used herein, "to treat" a condition or "treatment" of the condition is an approach for obtaining beneficial or desired results, such as clinical results. Beneficial or desired results can include, but are not limited to, alleviation or amelioration of one or more symptoms or conditions; diminishment of extent of disease, disorder, or condition; stabilized (i.e., not worsening) state of disease, disorder, or condition; preventing spread of disease, disorder, or condition; delay or slowing the progress of the disease, disorder, or condition; amelioration or palliation of the disease, disorder, or condition; and remission (whether partial or total), whether detectable or undetectable. "Palliating" a disease, disorder, or condition means that the extent and/or undesirable clinical manifestations of the disease, disorder, or condition are lessened and/or time course of the progression is slowed or lengthened, as compared to the extent or time course in the absence of treatment.

For administration to animal or human subjects, the pharmaceutical compositions comprise an effective dosage amount of tofacitinib or a pharmaceutically acceptable salt thereof. The formulation may be prepared using conventional methods, for example, depending on the subject to be treated, the mode of administration, and the type of treatment desired (e.g., prevention, prophylaxis, or therapy).

The dosage levels can be dependent on the nature of the condition, drug efficacy, the condition of the patient, the judgment of the practitioner, and the frequency and mode of administration. The doses can be administered to achieve any daily amount described herein, such as by administering one to five times daily (e.g., one, two, three, four, or five times daily).

"Effective amount" according to the disclosure is the amount of a drug sufficient to treat, prevent, or ameliorate a condition in a subject or patient. The effective amount of tofacitinib or pharmaceutically acceptable salt thereof, used to practice the present invention for therapeutic management of a condition may be determined and adjusted by a person of ordinary skill to provide the appropriate amount and dosage regimen, e.g., depending upon one or more of the manner of administration, the age, body weight, sex, and/or general health of the patient.

In an embodiment, the pharmaceutical compositions of the present invention were subjected to freeze-thaw cycle testing to determine stability, phase separation or precipitation or crystallization under high and low temperature conditions. Freeze-thaw testing is conducted by exposing the compositions filled in centrifuge tube to freezing temperatures (−20° C.) for at least 8 hours, and then samples were kept at 25° C. for at least 8 hours. This process is referred to as one Freeze-thaw cycle. Samples were subjected to at least 1 to 5 Freeze-thaw cycles and the samples were analyzed visually for particles or crystals.

Preparation of 0.1 N NaOH. 0.4 gm of sodium hydroxide (NaOH) pellet was added to 50 mL of purified water in volumetric flask and stirred to completely dissolve NaOH. 20 mL of purified water was added to the obtained solution and stirred. Volume was made up to 100 mL with purified water and mix solution thoroughly. Keep the solution for at least 1 hour at room temperature.

HPLC procedure for analysis of samples. The samples withdrawn from the different compositions at different storage conditions were analyzed for impurity profile using the following HPLC procedure. The materials and general conditions are listed below:

TABLE 1

| Chromatographic conditions | |
|---|---|
| Column | Sunfire C18, 250 × 4.6 mm, 5µ (Part No: 186002560) |
| Column temperature | 35° C. |
| Sample temperature | 25° C. |
| Injection volume | 20 L |
| Flow rate | 1.0 mL/min |
| Detection | 286 & 230 nm for Amino Pyrimidine |
| Run Time | 85 min |
| Mode of elution | Gradient |
| Needle Wash | Water:Acetonitrile: 20:80 % v/v |

TABLE 2

| Gradient program | | |
|---|---|---|
| Time (min) | % A | % B |
| 0.01 | 95 | 5 |
| 25 | 85 | 15 |
| 30 | 80 | 20 |
| 40 | 75 | 25 |
| 55 | 65 | 35 |
| 60 | 60 | 40 |
| 65 | 50 | 50 |
| 70 | 40 | 60 |
| 75 | 20 | 80 |
| 78 | 95 | 5 |
| 85 | 95 | 5 |

HPLC procedure for analysis of samples. The samples withdrawn from the different compositions at different storage conditions were analyzed for assay for tofacitinib using the following HPLC procedure. The materials and general conditions are listed below:

TABLE 3

| Chromatographic conditions | | | |
|---|---|---|---|
| Column | Kinetex XB C18, 100 A°, 150 × 4.6 mm, 2.6µ (Part no: 00F-44496-E0) | | |
| Column Temperature | 30° C. | | |
| Sample Temperature | 25° C. | | |
| Detector Wavelength | 220 nm with PDA/UV detector | | |
| Pump Mode | Gradient | | |
| Flow Rate | 0.8 mL/minutes | | |
| Injection Volume | 10 µL | | |
| Retention time | 18 minutes | | |
| Needle Wash | Water:Acetonitrile 20:80 % v/v | | |
| Gradient Table | Time (min) | % A | % B |
| | 0.01 | 60 | 40 |
| | 8 | 60 | 40 |

TABLE 3-continued

Chromatographic conditions

| | | |
|---|---|---|
| 10 | 10 | 90 |
| 12 | 10 | 90 |
| 13 | 60 | 40 |
| 18 | 60 | 40 |

EXAMPLES

The following examples are exemplary and not intended to be limiting. The above disclosure provides many different embodiments for implementing the features of the invention, and the following examples describe certain embodiments. It will be appreciated that other modifications and methods known to one of ordinary skill in the art can also be applied to the following experimental procedures, without departing from the scope of the invention.

Example 1. The Composition of Tofacitinib Solutions are Set Forth Below in Table 4

TABLE 4

| Ingredients | Composition-1 | Composition-2 | Composition-3 |
|---|---|---|---|
| | Quantity in mg/batch (Batch size - 100 mL) | | |
| Tofacitinib citrate* | 161.6 mg | 161.6 mg | 161.6 mg |
| HP-β-CD | 1000 mg | 1000 mg | 1000 mg |
| Tartaric acid | 100 mg | — | — |
| Sodium sulfite | — | 100 mg | — |
| Sodium metabisulfite | — | — | 200 mg |
| Purified water | q.s. to 100 mL | q.s. to 100 mL | q.s. to 100 mL | q.s.: quantity sufficient
*Note:
161.6 mg of tofacitinib citrate equivalent to 100 mg of tofacitinib Manufacturing procedure of Composition-1, 2 and 3: About 90 mL of the purified water was taken in manufacturing vessels. 1 g of HP-β-CD was added to each manufacturing vessel and stirred for 5-10 minutes to obtain clear solutions. 161.6 mg of tofacitinib citrate was added to each manufacturing vessel and stirred continuously for 15 minutes to obtain clear solutions. As mentioned in Table 4, specified quantities of tartaric acid, sodium sulfite and sodium metabisulfite were added to Composition-1, 2 and 3 respectively and stirred for 5-10 minutes to obtain clear solutions. Sufficient quantities of purified water were added to make up volumes to 100 mL. Room temperature condition was maintained throughout the preparation of solutions.

Samples of Composition 1, 2 and 3 were stored and analyzed at stress conditions (i.e., 40° C./75% RH condition and 60° C. condition). Samples of Composition-1, 2 and 3 were stored for 7 days at 40° C./75% relative humidity (RH) condition as well as for 5 days at 60° C. conditions, Tofacitinib Citrate remains solubilized and compositions were found to be clear without any recrystallization or precipitation. Initial samples of Composition-1, 2 and 3 were also subjected to freeze thaw cycling and observed for any visible particles or crystals by visual observation. No visible particles or crystal particles were observed in Composition-1, 2 and 3 after five freeze thaw cycles. Samples of Composition-1, 2 and 3 were analyzed for impurity profile, which were stored for 7 days at 40° C./75% RH condition and for 5 days at 60° C. conditions and data given in the below Table 5.

TABLE 5

| | Composition-1 | | Composition-2 | | Composition-3 | |
|---|---|---|---|---|---|---|
| | | | Condition | | | |
| | 60° C. | 40° C./75% RH | 60° C. | 40° C./75% RH | 60° C. | 40° C./75% RH |
| | | | Duration | | | |
| | 5 Days | 7 Days | 5 Days | 7 Days | 5 Days | 7 Days |
| Pack | Centrifuge tube (Polyvinyl chloride (PVC)) | | | | | |
| Visual observation of solution | Clear | Clear | Clear | Clear | Clear | Clear |
| | Impurities (% w/w) | | | | | |
| Pyrrolo Pyrimidine Impurity | 0.07 | 0.08 | 0.05 | 0.06 | 0.04 | 0.05 |
| Impurity-A | 0.01 | 0.01 | 0.01 | 0.01 | 0.01 | 0.01 |
| Impurity-B | 0.65 | 0.17 | 0.06 | ND | 0.16 | 0.12 |
| N-Oxide Impurity | 0.01 | 0.01 | 0.16 | ND | 0.04 | ND |
| Amino Pyrimidine Impurity | 0.01 | 0.01 | 0.05 | 0.02 | 0.03 | 0.02 |
| Ethyl Ester Impurity | 0.01 | ND | 0.01 | 0.01 | 0.02 | ND |
| Total Unknown Impurity (at RRT) | 0.02 (1.95) | 0.02 (1.62) | 3.83 (0.48) | 6.21 (0.48) | 3.74 (1.02) | 1.10 (0.48) |
| Total impurities | 0.85 | 0.36 | 11.77 | 18.24 | 12.21 | 3.60 |

Example 2. The Compositions of Tofacitinib Solutions are Set Forth Below in Table 6

TABLE 6

| | Composition | | | | | |
|---|---|---|---|---|---|---|
| | 4 | 5 | 6 | 7 | 8 | 9 |
| | Batch size | | | | | |
| | 1 L | 3 L | 1 L | 1 L | 1 L | 1 L |
| Ingredients | Quantity (mg/mL) | | | | | |
| Tofacitinib Citrate | 1.620* | 1.620* | 1.620* | 1.620* | 1.620* | 1.620* |
| Sodium Benzoate | 2.000 | 2.000 | 2.000 | 2.000 | 2.000 | 2.000 |
| Grape flavor | 2.000 | 2.000 | 2.000 | 2.000 | 2.000 | 2.000 |
| Sucralose | 3.000 | 3.000 | 3.000 | 3.000 | 3.000 | 3.000 |
| Tartaric Acid | 0.500 | 0.500 | 0.500 | 0.500 | 0.500 | — |
| Sodium Acetate | 1.000 | 1.000 | 1.000 | 1.000 | 1.000 | up to 1 mL |
| Purified Water | q.s. up to 1 mL | q.s. up to 1 mL | q.s. up to 1 mL | q.s. up to 1 mL | q.s. up to 1 mL | — |
| pH of final composition | 4.0 | 4.25 | 4.5 | 4.8 | 5.0 | 3.7 |

*1.620 mg of tofacitinib citrate is equivalent to 1 mg of tofacitinib

Manufacturing procedure of Composition-4, 6, 7 and 8: 950 mL of purified water was dispensed into suitable container. 0.5 gm of tartaric acid was added to purified water and continuous stirred at 25° C.±5° C. to obtain a solution-1. 1.62 gm of tofacitinib citrate was added to solution-1 and continuous stirred at 25° C.±5° C. to obtain a solution-2. 1 gm of sodium acetate was added to solution-2 and continuous stirred at 25° C.±5° C. to obtain a solution-3. 2 gm of sodium benzoate was added to solution-3 and continuous stirred at 25° C.±5° C. to obtain a solution-4. 3 gm of sucralose was added to solution-4 and continuous stirred at 25° C.±5° C. to obtain a solution-5. 2 gm of Grape flavor was added to solution-5 and continuous stirred at 25° C.±5° C. to obtain a solution-6. Required quantity of purified water was added to solution-6 to make up volume up to 980 mL and mixed for 10 minutes to solution-7. pH of solution-7 was adjusted by adding required quantity of 1N HCl. Purified water was added to the pH adjusted solution to make up volume up to 1000 mL and mixed for next 10 minutes to obtain final solution. The above described manufacturing procedure is same for Composition-32, 34, 35, 36 except the 1N HCl quantity required to obtain different pH values (i.e., 4.0, 4.5, 4.8 & 5.0 respectively) for the compositions.

Manufacturing procedure of Composition-5: 2850 mL of purified water was dispensed into suitable container. 1.5 gm of tartaric acid was added to purified water and continuous stirred at 25° C.±5° C. to obtain a solution-1. 4.848 gm of tofacitinib citrate was added to solution-1 and continuous stirred at 25° C.±5° C. to obtain a solution-2. 3 gm of sodium acetate was added to solution-2 and continuous stirred at 25° C.±5° C. to obtain a solution-3. 6 gm of sodium benzoate was added to solution-3 and continuous stirred at 25° C.±5° C. to obtain a solution-4. 9 gm of sucralose was added to solution-4 and continuous stirred at 25° C.±5° C. to obtain a solution-5. 6 gm of Grape flavor was added to solution-5 and continuous stirred at 25° C.±5° C. to obtain a solution-6. Required quantity of purified water was added to solution-6 to make up volume up to 2940 mL and mixed for 10 minutes to solution-7. pH of solution-7 was adjusted to 4.25 by adding required quantity of 1N HCl. Purified water was added to the pH adjusted solution to make up volume up to 3000 mL and mixed for next 10 minutes to obtain final solution with pH value 4.25.

Manufacturing procedure of Composition-9: 950 mL of pH 4.5 acetate buffer was dispensed into suitable container. 1.62 gm of tofacitinib citrate was added to acetate buffer and continuous stirred at 40° C.±2° C. to obtain a solution-1. 2 gm of sodium benzoate was added to solution-1 and continuous stirred at 25° C.±5° C. to obtain a solution-2. 3 gm of sucralose was added to solution-2 and continuous stirred at 25° C.±5° C. to obtain a solution-3. 2 gm of Grape flavor was added to solution-3 and continuous stirred at 25° C.±5° C. to obtain a solution-4. Required quantity of purified water was added to solution-4 to make up volume up to 980 mL and mixed for 10 minutes to solution-5. pH of solution-5 was adjusted to 3.7 by adding required quantity of 1N HCl. Purified water was added to the pH adjusted solution to make up volume up to 1000 mL and mixed for next 10 minutes to obtain final solution with pH value 3.7.

Example 3

TABLE 7

Stability data of Composition-4

| | | Composition-4 Condition | | | | |
|---|---|---|---|---|---|---|
| | | RT* | 40° C./ 75% RH | | 25° C.7 60% RH | |
| | | | Duration (in months) | | | |
| | | Initial | 3 | 6 | 3 | 6 |
| Description | | | Clear, Colourless solution | | | |
| pH of final solution | | 4.00 | 3.96 | 3.91 | 3.96 | 3.91 |
| Tofacitinib assay | | 99.7 | 104.5 | 99.3 | 103.2 | 100.4 |
| Impurity profile & Specification limit (NMT % w/w) | | | (% w/w) | | | |
| Impurity-B | 0.5% | 0.011 | 0.204 | 0.385 | 0.054 | 0.083 |
| Amino-pyrimidine Impurity | 0.5% | ND | ND | ND | ND | ND |
| Pyrrolo Pyrimidine Impurity | 0.5% | 0.103 | 0.093 | 0.092 | 0.096 | 0.096 |
| N-oxide Impurity | 0.5% | ND | ND | ND | ND | ND |
| 1-Amide Impurity | 0.5% | 0.002 | 0.006 | 0.009 | 0.003 | ND |
| Individual maximum unspecified impurity (RRT) | 0.2% | 0.022 (1.58) | 0.022 (1.54) | 0.021 (0.98) | 0.023 (1.54) | 0.013 (1.54) |
| Total Impurities | 3.0% | 0.191 | 0.368 | 0.531 | 0.214 | 0.192 |

*RT = Room Temperature; RRT = Relative Retention Time; NMT = Not More Than

TABLE 8

Stability data of Composition-5

| | | Composition-5 Condition | | | | |
|---|---|---|---|---|---|---|
| | | RT* | 40° C./75% RH | | 25° C./60% RH | |
| | | | Duration (in months) | | | |
| | | Initial | 3 | 6 | 3 | 6 |
| Description | | | Clear, Colourless solution | | | |
| pH of final solution | | 4.26 | 4.25 | 4.22 | 4.23 | 4.22 |
| Tofacitinib Assay | | 101.5 | 100.6 | 102.7 | 98.9 | 103.2 |
| Impurity profile & Specification limit (NMT % w/w) | | | (% w/w) | | | |
| Impurity-B | 0.5% | 0.021 | 0.146 | 0.309 | 0.034 | 0.066 |
| Amino-pyrimidine Impurity | 0.5% | ND | ND | ND | ND | ND |
| Pyrrolo Pyrimidine Impurity | 0.5% | 0.106 | 0.099 | 0.085 | 0.101 | 0.095 |
| N-oxide Impurity | 0.5% | ND | ND | ND | ND | ND |
| 1-Amide Impurity | 0.5% | ND | 0.005 | 0.008 | ND | ND |
| Individual maximum unspecified impurity (RRT) | 0.2% | 0.019 (1.58) | 0.020 (0.67) | 0.028 (0.98) | 0.018 (1.54) | 0.008 (1.77) |
| Total Impurities | 3.0% | 0.190 | 0.345 | 0.458 | 0.185 | 0.169 |

TABLE 9

Stability data of Composition-6

| | | Composition-6 Condition | | | | |
|---|---|---|---|---|---|---|
| | | RT* | 40° C./75% RH | | 25° C./60% RH | |
| | | | Duration (in months) | | | |
| | | Initial | 3 | 6 | 3 | 6 |
| Description | | Clear, Colourless solution | | | | |
| pH of final solution | | 4.52 | 4.48 | 4.43 | 4.49 | 4.42 |
| Tofacitinib Assay | | 100 | 101.8 | 99.2 | 102.6 | 99.7 |
| Impurity profile & Specification limit (NMT % w/w) | | | | (% w/w) | | |
| Impurity-B | 0.5% | 0.018 | 0.169 | 0.313 | 0.043 | 0.063 |
| Amino-pyrimidine Impurity | 0.5% | ND | ND | ND | ND | ND |
| Pyrrolo Pyrimidine Impurity | 0.5% | 0.156 | 0.100 | 0.100 | 0.100 | 0.102 |
| N-oxide Impurity | 0.5% | ND | ND | ND | ND | ND |
| 1-Amide Impurity | 0.5% | 0.003 | 0.006 | 0.009 | 0.003 | ND |
| Individual maximum unspecified impurity (RRT) | 0.2% | 0.03 (1.83) | 0.028 (0.99) | 0.042 (0.98) | 0.023 (1.54) | 0.014 (1.54) |
| Total Impurities | 3.0% | 0.301 | 0.392 | 0.539 | 0.238 | 0.205 |

TABLE 10

Stability data of Composition-7

| | | Composition-7 Condition | | | | |
|---|---|---|---|---|---|---|
| | | RT* | 40° C./75% RH | | 25° C./60% RH | |
| | | | Duration (in months) | | | |
| | | Initial | 3 | 6 | 3 | 6 |
| Description | | Clear, Colourless solution | | Particles observed | Particles observed | Particles observed |
| pH of final solution | | 4.80 | 4.73 | 4.79 | 4.69 | 4.69 |
| Tofacitinib Assay | | 96.7 | 97.4 | 96.9 | 29.9 | 29.6 |
| Impurity profile & Specification limit (NMT % w/w) | | | | (% w/w) | | |
| Impurity-B | 0.5% | 0.03 | 0.169 | Analysis not done as particles observed. | 0.03 | Analysis not done as particles observed. |
| Amino-pyrimidine Impurity | 0.5% | ND | ND | | ND | |
| Pyrrolo Pyrimidine Impurity | 0.5% | 0.085 | 0.095 | | 0.09 | |
| N-oxide Impurity | 0.5% | ND | ND | | ND | |
| 1-Amide Impurity | 0.5% | ND | 0.004 | | 0.001 | |
| Individual maximum unspecified impurity (RRT) | 0.2% | ND | 0.018 (0.18) | | 0.01 (0.63) | |
| Total Impurities | 3.0% | 0.11 | 0.353 | | 0.131 | |

TABLE 11

Stability data of Composition-8

| | | Composition-8 Condition | | | | |
|---|---|---|---|---|---|---|
| | | RT* | 40° C./75% RH | | 25° C./60% RH | |
| | | Duration (in months) | | | | |
| | | Initial | 3 | 6 | 3 | 6 |
| Description | | Clear, Colourless solution | | Particles observed | Particles observed | Particles observed |
| pH of final solution | | 5.00 | 4.88 | 4.81 | 4.81 | 4.85 |
| Tofacitinib Assay | | 100.5 | NA | NA | 38.7 | 22.3 |
| Impurity profile & Specification limit (NMT % w/w) | | | | (% w/w) | | |
| Impurity-B | 0.5% | 0.012 | 0.211 | | Analysis not done as particles observed. | |
| Amino-pyrimidine Impurity | 0.5% | ND | ND | | | |
| Pyrrolo Pyrimidine Impurity | 0.5% | 0.104 | 0.090 | | | |
| N-oxide Impurity | 0.5% | ND | ND | | | |
| 1-Amide Impurity | 0.5% | 0.002 | 0.008 | | | |
| Individual maximum unspecified impurity (RRT) | 0.2% | 0.010 (0.94) | 0.025 (0.98) | | | |
| Total Impurities | 3.0% | 0.152 | 0.410 | | | |

TABLE 12

Stability data of Composition-9

| | | Composition-9 Condition | | |
|---|---|---|---|---|
| | | RT* | 40° C./75% RH | 25° C./60% RH |
| | | Duration (in months) | | |
| | | Initial | 6 | 6 |
| Description | | Clear, Colourless solution | | |
| pH of final solution | | 3.70 | 3.79 | 3.80 |
| Tofacitinib Assay | | 98.5 | 99.2 | 100.1 |
| Impurity profile & Specification limit (NMT % w/w) | | | (% w/w) | |
| Impurity-B | 0.5% | 0.015 | 0.801 | 0.193 |
| Amino-pyrimidine Impurity | 0.5% | ND | ND | ND |
| Pyrrolo Pyrimidine Impurity | 0.5% | 0.099 | 0.064 | 0.086 |
| N-oxide Impurity | 0.5% | ND | ND | ND |
| 1-Amide Impurity | 0.5% | ND | 0.033 | 0.009 |
| Individual maximum unspecified impurity (RRT) | 0.2% | 0.009 (1.3) | 0.023 (0.98) | 0.013 (1.54) |
| Total Impurities | 3.0% | 0.155 | 0.97 | 0.317 |

Example 4. Tofacitinib Solutions Having Compositions were Set Forth in Table 13

TABLE 13

| Ingredients | Composition-10 | Composition-11 |
|---|---|---|
| | Quantity (mg/mL); Batch size = 1 L | |
| Tofacitinib citrate | 1.620* | 1.620* |
| Tartaric acid | — | 1.00 |
| HP-β-CD | 25.00 | 25.00 |
| Sodium benzoate | 2.000 | 2.000 |
| Mixed berry flavor | 2.000 | 2.000 |
| Sucralose | 3.000 | 3.000 |
| Purified water | up to 1 mL | up to 1 mL |

*1.620 mg of tofacitinib citrate is equivalent to 1 mg of tofacitinib

Manufacturing procedure of Composition-10. 950 mL of purified water was dispensed into suitable container and heated to 50° C.±2° C. 25 gm of HP-β-CD was added to purified water and continuous stirred at 50° C.±2° C. to obtain a solution-1. 1.62 gm of tofacitinib citrate was added to solution-1 and continuous stirred at 40° C.±2° C. to obtain a solution-2. 2 gm of sodium benzoate was added to solution-2 and continuous stirred at 35° C.±5° C. to obtain a solution-3. 3 gm of sucralose was added to solution-3 and continuous stirred at 25° C.±5° C. to obtain a solution-4. 2 gm of mixed berry flavor was added to solution-4 and continuous stirred at 25° C.±5° C. to obtain a solution-5. Required quantity of purified water was added to solution-5 to make up volume up to 1000 mL and mixed for 10 minutes to final solution.

Manufacturing procedure of Composition-11. 950 mL of purified water was dispensed into suitable container and heated to 50° C.±2° C. 25 gm of HP-β-CD was added to purified water and continuous stirred at 50° C.±2° C. to obtain a solution-1. 1.62 gm of tofacitinib citrate was added to solution-1 and continuous stirred at 40° C.±2° C. to obtain a solution-2. 2 gm of sodium benzoate was added to solution-2 and continuous stirred at 35° C.±5° C. to obtain a solution-3. 3 gm of sucralose was added to solution-3 and continuous stirred at 25° C.±5° C. to obtain a solution-4. 2 gm of mixed berry flavor was added to solution-4 and continuous stirred at 25° C.±5° C. to obtain a solution-5. 1 gm of tartaric was added to solution-5 and continuous stirred at 25° C.±5° C. to obtain a solution-6. Required quantity of purified water was added to solution-5 to make up volume up to 1000 mL and mixed for 10 minutes to final solution.

Oxidative stress testing: Composition-10 & 11 were exposed to oxidation stress conditions to observe oxidative impurity formation. Table 14 contains information of the two different oxidation stress conditions used to generate oxidative stress and total impurities profile of Composition-10 & 11 were compared under these conditions.

TABLE 14

Total Impurities data of Tofacitinib oral solution 1 mg/mL under oxidative stress

| | % Total Impurities | |
|---|---|---|
| Oxidative Stress Condition | Composition-10 | Composition-11 |
| Exposure of sample to 5% Hydrogen peroxide solution at 60° C. for 60 minutes | 1.95% | 0.57% |
| Exposure of sample to 30% Hydrogen peroxide solution at 60° C. for 60 minutes | 18.47% | 4.46% |

While the invention has been described above with reference to specific embodiments thereof, it is apparent that many changes, modifications, and variations can be made without departing from the inventive concept disclosed herein, and such description is not intended as limitations on the scope thereof. Accordingly, it is intended to embrace all such changes, modifications, and variations that fall within the spirit and broad scope of the appended claims.

The invention claimed is:

1. A stable solution of tofacitinib consisting essentially of:
    tofacitinib at a concentration of about 1 mg/mL, and optionally one or more antioxidants; and
    a pharmaceutically acceptable liquid vehicle selected from the group consisting of water, purified water, ethanol or a combination thereof;
    wherein pH of the solution ranges from 3.7 to 4.5;
    wherein the solution is free from precipitation when said solution is stored at 25° C./60% RH for at least 6 months;
    wherein level of total impurities in the solution is less than 1.5% w/w as measured by HPLC, when said solution is stored at 40° C./75% RH for 6 months;
    wherein said solution is a palatable oral solution.

2. The solution according to claim 1, said solution further comprising one or more other pharmaceutically acceptable excipients selected from the group consisting of stabilizers, solubilizers, pH adjusting agents, buffering agents, thickening agents, chelating agents, preservatives, flavoring agents, sweetening agents, coloring agents and mixtures thereof.

3. The solution according to claim 1, wherein the antioxidant is selected from the group consisting of sodium bisulfate, ascorbic acid, ascorbyl palmitate, citric acid, tartaric acid, glycine, L-cysteine hydrochloride, L-methionine, butylated hydroxy anisole (BHA), butylated hydroxytoluene (BHT), hydro phosphorous acid, monothioglycerol, propyl gallate, sodium ascorbate, sodium citrate anhydrous, sodium citrate dihydrate, sodium sulfide, sodium sulfite, sodium bisulfite, sodium formaldehyde sulfoxylate, thioglycolic acid and sodium metabisulfite.

4. The solution according to claim 1, wherein the concentration of the anti-oxidant ranges from about 0.01% to about 50% w/w of the solution.

5. The solution according to claim 1, wherein the anti-oxidant is present at a concentration of about 0.05% w/w of the solution.

6. The solution according to claim 1, wherein the anti-oxidant is tartaric acid.

7. The solution according to claim 6, wherein the tartaric acid is present in the concentration of about 0.05% w/w of the solution.

8. The solution according to claim 6, wherein the tartaric acid is present in an amount of 0.5 mg/mL.

9. The solution according to claim 1, wherein the weight ratio of the anti-oxidant to tofacitinib is from about 0.1:1 to about 1:10.

10. A stable solution of tofacitinib consisting essentially of: tofacitinib at a concentration of about 1 mg/mL, and optionally one or more antioxidants;
- a pharmaceutically acceptable liquid vehicle selected from the group consisting of water, purified water, ethanol or a combination thereof;
- wherein pH of the solution ranges from 3.7 to 4.5;
- wherein the solution is free from precipitation when said solution is stored at 25° C./60% RH for at least 6 months;
- wherein level of total impurities in the solution is less than 1.5% w/w as measured by HPLC, when said solution is stored at 40° C./75% RH for 6 months;
- wherein said solution is a palatable oral solution and wherein said oral solution further comprises one or more other pharmaceutically acceptable excipients selected from the group consisting of stabilizers, solubilizers, pH adjusting agents, buffering agents, thickening agents, chelating agents, preservatives, flavoring agents, sweetening agents, coloring agents and mixtures thereof.

\* \* \* \* \*